United States Patent [19]

D'Alò

[11] 4,131,615
[45] Dec. 26, 1978

[54] FURAN DERIVATIVE FOR USE AS PHARMACEUTICAL PRODUCT PARTICULARLY FOR THE TREATMENT OF RHEUMATIC ILLNESSES

[75] Inventor: Giorgio D'Alò, Milan, Italy

[73] Assignee: A. Wasserman S.p.A., Milan, Italy

[21] Appl. No.: 822,863

[22] Filed: Aug. 8, 1977

[51] Int. Cl.² .................................... C07D 307/54
[52] U.S. Cl. .......................... 260/347.3; 260/347.4; 424/285
[58] Field of Search ..................... 260/347.3, 347.4; 424/285

[56] References Cited

U.S. PATENT DOCUMENTS

| | | | |
|---|---|---|---|
| 3,257,420 | 6/1966 | Szarvasi et al. | 260/347.4 |
| 3,655,693 | 4/1972 | Shen et al. | 260/347.3 X |
| 4,000,164 | 12/1976 | Parker | 260/347.4 |

Primary Examiner—Richard Raymond

Attorney, Agent, or Firm—Sughrue, Rothwell, Mion, Zinn and Macpeak

[57] ABSTRACT

Furan Derivatives Having the Formula

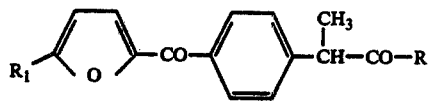

in which:
$R_1$ is a hydrogen or bromine atom,
$R$ is —OH, —OCH$_3$, or

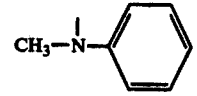

and use thereof in the treatment of rheumatic illnesses.

3 Claims, No Drawings

FURAN DERIVATIVE FOR USE AS PHARMACEUTICAL PRODUCT PARTICULARLY FOR THE TREATMENT OF RHEUMATIC ILLNESSES

The present invention relates to pharmaceutial products and particularly to pharmaceutical products having a specific analgesic, anti-inflammatory or anti-pyretic activity and to those useful in the treatment of rheumatic illnesses.

According to one aspect of the present invention, there is provided a pharmaceutical product consisting of a derivative of 4-(furan-2-carbonyl) phenylacetic acid having the formula:

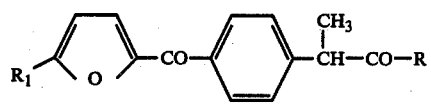

in which:
$R_1$ is a hydrogen or bromine atom,
R is —OH, —OCH$_3$,

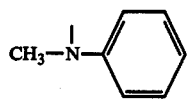

In a preferred embodiment of the invention the pharmaceutical product is
±α-methyl-4-(furan-2-carbonyl) phenylacetic acid having the formula:

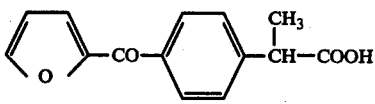

preferably as its salt formed with an alkali or alkaline earth metal.

According to a further aspect of the present invention there is provided a method for the preparation of the compounds according to the formula:

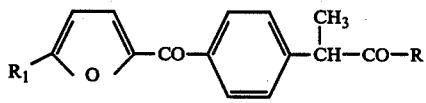

in which:
$R_1$ is a hydrogen or bromine atom,
R is —OH, —OCH$_3$,

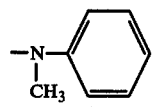

which includes the following steps:
a) reaction of a 4-halophenyl-furan-2-ketone according to the formula:

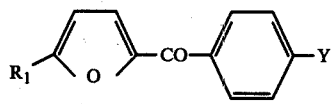

in which $R_1$ has the same significations as above, and in which Y is a halogen atom, with the sodium derivative of the diethyl ester of a methyl-malonic acid having the formula $CH_3$—$CH(CO_2H)_2$, in the presence of an aprotic solvent, to obtain diethylester of 2-methyl-2-[4-(furan-2-carbonyl)phenyl]malonic acid;

b) saponification of the diethyl ester obtained in stage a) and separation of the resulting salt, and c) acidification of the salt obtained in stage b) to obtain the required acid.

The aprotic solvent used in stage a) is preferably dimethyl formamide, dimethyl sulphoxide or hexamethyl phosphortriamide.

The diethyl ester of the methyl-malonic acid formed in stage a) will have the formula:

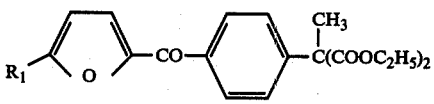

where $R_1$, has the same significations as above.

The preparation of pharmaceutical products according to the invention will now be more particulary described, by way of examples

EXAMPLE 1

To 200 cc of hexamethylphosphortriamide are added: 10 g (about 0.2 mol.) of a 50% suspension in oil of sodium hydride which has previously been washed with benzene, and 34.8 g (0.2 mol.) of the diethyl ester of 2-methyl malonic acid, which is added slowly, drop by drop. The reagent mixture is agitated at room temperature for 1 hour then cooled with water and ice.

36 g (0.189 mol.) of 4-fluorophenyl-furan-2-ketone are then added portionwise. The resulting mixture is agitated for a further hour at room temperature then heated over a water bath for 17 hours.

After cooling, the mixture is diluted with 600 cc of benzene, water is added and the benzene layer is separated.

A further quantity of benzene is added to the mother liquor and the benzene layer is again separated and added to that from the previous separation. The total benzene extracts are then washed with water, dried on sodium sulphate and concentrated under vacuum.

The residue is distilled and fractions containing unreacted malonic ester and 4-fluorophenyl-furan-2-ketone and the required diethyl ester of 2-methyl-2[4-(furan-2-carbonyl)phenyl]malonic acid having $Kp_{0.2}$ at 199°–210° C. are collected. 36.5 g, that is 56% of the theoretical quantity, of the required product are obtained. By including the reclaimable material, returns of even 80–85% of the theoretical can be achieved. The product, when tested by gas-chromatography, is found to be sufficiently pure.

43 g of the diethyl ester of 2-methyl-2[4-(furan-2-carbonyl)phenyl]malonic acid (0.125 mol.) are treated at room temperature with 95 cc of a 15% solution of potassium hydroxide in methyl alcohol (0.250 mol.). The reaction is allowed to continue at room temperature for 3 days, and the products are then poured into a water and ice mixture and extracted with ether, giving ether extract (1).

The aqueous solution remaining is acidified with hydrochloric acid, diluted and the oily precipitate is extracted with ether. The ethereal solution is dried with sodium sulphate and evaported. The residue obtained is dissolved in a bicarbonate solution, extracted with ether, giving ether extract (2), and the aqueous solution is acidified with hydrochloric acid, diluted and placed in a refrigerator.

The product solidifies as a solid mass which is crumbled and subjected to suction in a vacuum.

After drying in an oven at 40° C., the product is crystallized twice from isopropyl ether, the ±α-methyl-4-(furan-2-carbonyl)-phenylacetic acid being obtained, having a melting point of 86° C.-88° C.

12 g, that is 68% of the theoretical quantity, are obtained.

19 g of the diethyl ester of 2-methyl-2-[4-(furan-2-carbonyl) phenyl]malonic acid are recovered from the ether extracts (1) (2).

EXAMPLE 2

34.4 g (0.1 mol.) of diethylester of 2-methyl-2[4-(furan-2-carbonyl)phenyl]malonic acid and a catalytic amount of red phosphorus are dissolved in 200 cc of chloroform.

95 cc of bromine ($Br_2$) are added dropwise to said solution maintained at boiling temperature.

The reaction is allowed to continue at room temperature for 2 days. The reaction product is then washed with water, successively with $NaHCO_3$ solution and finally with water.

33 g of diethylester of 2-methyl-2[4-(5-bromofuran-2-carbonyl)-phenyl]-malonic acid having $Kp_{0.8-1}$ at 228°-231° C. are obtained from the said dried chloroform solution by a vacuum distillation step.

The diehtylester of 2-methyl-2[4-(5-bromofuran-2-carbonyl)phenyl]-malonic acid is treated at room temperature with a KOH methyl alcoholic solution according to the same method of the EXAMPLE 1, whereby ±α-methyl-4-(5-bromofuran-2-carbonyl)-phenylacetic acid is obtained. (M.P. 108°-110° C.).

EXAMPLE 3

The ±α-methyl-4-(furan-2-carbonyl)-phenylacetic acid of the EXAMPLE 1 is neutralized with a stoichiometric amount of $NaHCO_3$.

An aqueous concentrated solution of $CaCl_2$ is added to an aqueous solution of the sodium salt of the said acid.

A precipitate consisting of Ca salt of the said acid is obtained.

This precipitate is under vacuum sucked, washed with iced water, dissolved in methyl alcohol and crystalized from the alcoholic solution.

By a successive crystallisation from the same methylalcoholic solvent, a Ca salt of the said acid is obtained which has the desired Ca content (7.61% b.w.) and, when tested by chromatographic analysis on thin layer, is pure.

EXAMPLE 4

The ±α-methyl-4-(furan-2-carbonyl)-phenylacetic acid of the EXAMPLE 1 is treated with thionil chloride. Successively methyl ester is obtained by a reaction of the thionil chloride of the said acid with methyl alcohol.

The product crystallized from the corresponding ethyl alcoholic solution has a M.P. of 58°-59° C.

EXAMPLE 5

The same product obtained in the EXAMPLE 4, is prepared by a reaction of ±α-methyl-4-(furan-2-carbonyl)-phenylacetic acid with an ethereal solution of diazomethane.

EXAMPLE 6

N-methylanilide of the ±α-methyl-5-(furan-2-carbonyl)-phenylacetic acid is obtained from a reaction of the chloride of the said acid with N-methylaniline.

The product crystallized from the corresponding hexane solution has a M.P. of 90°-91° C.

The product of the EXAMPLE 1, ±αmethyl-4-(furan-2-carbonyl)phenyl acetic acid, was subjected to toxicological and pharmacological tests in rats and mice. The animals used were Sprague Dawley rats and Swiss mice of both sexes, to which the product was administered orally as a 2% suspension in gum arabic parenterally as the sodium salt.

TEST CARRIED OUT:

1) Acute oral toxicity.

This has been tested in male and female mice weighing from 18 to 22 g and in female rats weighing from 90 to 120 grams.

The product was administered to groups of 6 mice and groups of 6 rats, mortality being looked for 14 days after the administration.

The approximate values of $LD_{50}$ are:
1000 mg/Kg in the mouse:
980(817–1175)-mg/Kg in the rat.

2) Anti-inflammatory activity.

An edema was induced in male rats weighing about 120 grams by injection into the aponeurosis under the plantaris of the left foot of 0.1 ml of 1% Carrageenan in saline.

The oral administration of 80-40-20 mg/Kg of product, 30 minutes before the inflammatory agent, reduced after 3 hours the development of the edema by rispectively 53%-47% -23% with respect to that induced in the controls.

Similar results are obtained with respect to the reduction of the subplantaris inflammation induced by 0,1 ml of a 5% Kaolin in saline.

The administration of product doses equals to those above cited induce in the rat a regress of the Nystatin subplantaris edema (curative activity).

3) Anti-inflammatory activity on Cotton-Pellet induced granuloma.

The oral administration daily for 7 days of a dose of 15 mg/Kg of the product, divided into 4 administrations taken over a time of 9 hours, reduced the formation of granulomatous tissue formed around Cotton-Pellets planted aseptically under the skin of female rats, weighing from 180 to 200 grams, by 17% with respect to controls.

4) Analgesic activity.

The oral administration of the product to female mice weighing from 18 to 22 grams reduced the number of contortions caused by the intraperitoneal injection of 0.1 ml/10 g of body weight of a 0.02% solution of phenyl-p-benzoquinone.

The $ED_{50}$ value is 4.35 mg/Kg.

5) Antipyretic Effect in Yeast-Induced fever.

The oral administration of rispectively 80-40-20 mg/Kg of the product to female rats reduces the increase in temperature of the rectum, caused by the injection under the skin of 10 ml/Kg of 15% brewer's yeast in 1% arabic gum, by rispectively 71%-63%-33% after 60 minutes (peak-effect) from the administration.

6) Recovery from experimentally induced arthritis in the rat (Freund's adjuvant arthritis) has been obtained with oral administration of 20-40 mg/Kg as confirmed successively by radiologic test of the affected articulations.

7) Action on arterial pressure.

The endovenous injection of doses of the product (2.5-12.5-62.5 mg/Kg) in a rabbit does not induce significant variations in the blood pressure.

What we claim is:

1. A derivate of 4-(furan-2-carbonyl) phenylacetic acid having formula

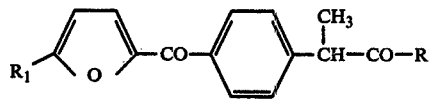

in which:
$R_1$ is a hydrogen or bromine atom,
R is —OH, —OCH$_3$, or

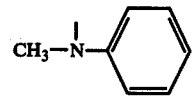

2. A compound according to claim 1, consisting of ±α-methyl-4-(furan-2-carbonyl)phenylacetic acid having the formula

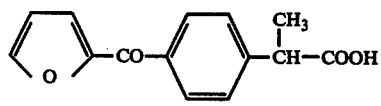

3. A compound according to claim 1 consisting of an alkali or alkaline earth salt of the ±α-methyl-4-(furan-2-carbonyl) phenyl acetic acid.

* * * * *

UNITED STATES PATENT AND TRADEMARK OFFICE
CERTIFICATE OF CORRECTION

PATENT NO. : 4,131,615
DATED : December 26, 1978
INVENTOR(S) : Giorgio D'ALO

It is certified that error appears in the above-identified patent and that said Letters Patent are hereby corrected as shown below:

IN THE HEADING:

Foreign Application Priority Data:

Insert -- Aug. 6, 1976  Great Britain........32929/76 --

Signed and Sealed this

Third Day of April 1979

[SEAL]

Attest:

RUTH C. MASON
*Attesting Officer*

DONALD W. BANNER
*Commissioner of Patents and Trademarks*